United States Patent [19]

Lee et al.

[11] Patent Number: 5,202,516

[45] Date of Patent: Apr. 13, 1993

[54] PROCESS OF RECOVERING MONOALKYLBENZENE AND PURE 1,3,5-TRIALKYBENZENE FROM A MIXTURE OF DIALKYL-AND TRIALKYLBENZENES

[75] Inventors: Guo-shuh J. Lee; Michael M. Olken; Juan M. Garces, all of Midland; Garmt R. Meima, Terneuzen, Netherlands

[73] Assignee: The Dow Chemical Company, Midland, Mich.

[21] Appl. No.: 747,172

[22] Filed: Aug. 19, 1991

Related U.S. Application Data

[63] Continuation-in-part of Ser. No. 718,741, Jun. 21, 1991, which is a continuation-in-part of Ser. No. 689,411, Apr. 22, 1991, which is a continuation-in-part of Ser. No. 455,677, Dec. 22, 1989, which is a continuation-in-part of Ser. No. 323,530, Mar. 14, 1989, Pat. No. 5,004,841, which is a continuation-in-part of Ser. No. 123,741, Nov. 23, 1987, Pat. No. 4,891,448.

[51] Int. Cl.$^5$ .............. C07C 4/18; C07C 7/12
[52] U.S. Cl. .............. 585/467; 585/475; 585/804; 585/805; 585/800; 585/831
[58] Field of Search .............. 585/826, 828, 823, 821, 585/820, 831, 446, 451, 467, 468, 478, 477, 474, 475, 805, 804, 800

[56] References Cited

U.S. PATENT DOCUMENTS

| | | | |
|---|---|---|---|
| 3,114,782 | 12/1963 | Fleck et al. .............. | 585/826 |
| 3,268,607 | 8/1966 | Schmitt et al. .............. | 260/668 |
| 3,629,351 | 12/1971 | Olive et al. .............. | 260/672 T |
| 3,761,396 | 9/1973 | Pickert .............. | 208/111 |
| 3,763,259 | 10/1973 | Hervert .............. | 260/671 P |
| 3,763,260 | 10/1973 | Pollitzer et al. .............. | 260/672 T |
| 3,780,122 | 9/1973 | Pollitzer .............. | 260/672 T |
| 3,849,340 | 11/1974 | Pollitzer et al. .............. | 252/455 Z |
| 3,864,416 | 2/1975 | Campbell et al. .............. | 260/674 A |
| 3,894,109 | 7/1975 | Rosback .............. | 260/674 SA |
| 3,943,183 | 3/1976 | Rosback .............. | 260/674 SA |
| 4,044,062 | 8/1977 | Korous et al. .............. | 260/674 SA |
| 4,046,827 | 6/1977 | Owen et al. .............. | 260/672 T |
| 4,051,192 | 9/1977 | Neuzil et al. .............. | 260/674 SA |
| 4,083,886 | 4/1978 | Michalko .............. | 260/672 T |
| 4,107,086 | 8/1978 | Michalko .............. | 252/455 Z |
| 4,283,587 | 8/1981 | Rosback et al. .............. | 585/828 |
| 4,482,777 | 11/1984 | Neuzil .............. | 585/828 |
| 4,542,254 | 9/1985 | Santacesaria et al. .............. | 585/828 |
| 4,717,778 | 1/1988 | Zinnen et al. .............. | 568/934 |
| 4,743,708 | 5/1988 | Rosenfeld et al. .............. | 585/828 |
| 4,774,377 | 9/1988 | Barger et al. .............. | 585/323 |
| 4,864,069 | 9/1989 | Zinnen .............. | 585/828 |

FOREIGN PATENT DOCUMENTS 078639  1/1980  Japan .............. 585/828

OTHER PUBLICATIONS

Derwent 7804S-E (BE 768130-Q/1971).

*Primary Examiner*—Marianne M. Cintins
*Assistant Examiner*—Margaret J. Page

[57] ABSTRACT

A process of recovering monoalkylbenzene and pure 1,3,5-trialkylbenzene from an isomeric mixture containing dialkyl- and trialkylbenzenes. The process comprises transalkylating a monocyclic aromatic compound with a mixture of dialkyl- and trialkyl-benzenes in the presence of an acidic mordenite zeolite under conditions such that monoalkylbenzene and predominantly 1,3,5-trialkylbenzene are formed. 1,3,5-trialkylbenzene is isolated in pure form from a mixture of the same and 1,2,4- and/or 1,2,3-trialkylbenzene by use of a dealuminated zeolite Y adsorbent.

20 Claims, No Drawings

PROCESS OF RECOVERING MONOALKYLBENZENE AND PURE 1,3,5-TRIALKYBENZENE FROM A MIXTURE OF DIALKYL-AND TRIALKYLBENZENES

CROSS-REFERENCE TO RELATED APPLICATIONS

This application is a continuation-in-part of co-pending Application Ser. No. 718,741, filed Jun. 21, 1991, which is a continuation-in-part of co-pending Application Ser. No. 689,411, filed Apr. 22, 1991, which is a continuation-in-part of co-pending Application Ser. No. 455,677, filed Dec. 22, 1989, which is a continuation-in-part of co-pending Application Ser. No. 323,530, filed Mar. 14, 1989, now U.S. Pat. No. 5,004,841, which is a continuation-in-part of Application Ser. No. 123,741, filed Nov. 23, 1987, now U.S. Pat. No. 4,891,448.

BACKGROUND OF THE INVENTION

This invention relates to a process of recovering monoalkylbenzene and pure 1,3,5-trialkylbenzene from an isomeric mixture of dialkyl- and trialkylbenzenes.

Dialkylbenzenes are useful transalkylating agents in the transalkylation of benzene to valuable monoalkylated benzenes, such as ethylbenzene and cumene. Cumene, also known as isopropylbenzene, is useful for the production of phenol, acetone and alpha-methylstyrene. Ethylbenzene is useful in the production of styrene.

1,3,5-trialkylbenzenes, such as 1,3,5-triisopropylbenzene, are useful as high temperature solvents and as starting materials for the synthesis of agricultural chemicals. 1,3,5-Triethylbenzene is also useful as a starting material for the synthesis of K-resins.

U. S. Pat. No. 4,774,377 discloses the transalkylation of benzene by dialkylated aromatic compounds to monoalkylated aromatic compounds in the presence of an acidic mordenite zeolite catalyst. Disadvantageously, the dialkylated isomer is required to be essentially pure and may not contain significant quantities of trialkylated isomer, because the latter plugs the catalysts' pores and quickly deactivates the catalyst. Accordingly, U.S. Pat. No. 4,774,377 teaches a costly separation via fractional distillation of the trialkylated and dialkylated mixture prior to the transalkylation step.

1,3,5-trialkylbenzenes are prepared by the alkylation of benzene. Catalysts therefor, such as solid phosphoric acid and acidic zeolites, are well known in the art. U.S. Pat. No. 3,761,396, for example, teaches such a process using super-siliceous zeolites as catalysts, such as dealuminated Y, X, L, omega and synthetic mordenite. The examples illustrate the use of these catalysts in the alkylation of benzene with propylene to yield a mixture of mono, di-, and triisopropylbenzenes.

The problem with the above-identified alkylation is that 1,3,5-trialkylbenzene is obtained in a product mixture with 1,2,4-trialkylbenzene and three dialkylbenzene isomers. Typically, the 1,2,3-trialkylated isomer is not obtained in significant quantity. The dialkylbenzenes are usually separated from the trialkylbenzenes by distillation: however, 1,3,5- and 1,2,4-trialkylbenzenes cannot be separated by distillation because their boiling points are too close. Thus, 1,3,5-trialkylbenzene cannot be obtained in high purity by methods known in the art. Moreover, in order to recover the commercial value of the dialkylbenzenes, their isomeric mixture must be separated by further distillation, or alternatively, transalkylated to useful monoalkylbenzenes.

Other syntheses of 1,3,5-trialkylbenzenes have been reported. For example, U.S. Pat. No. 3,268,607 teaches a process comprising contacting benzene with propylene and/or cumene, diisopropylbenzene or triisopropylbenzene in the presence of an acid-activated clay to obtain a product mixture containing predominantly 1,3,5-triisopropylbenzene and 1,2,4,5-tetraisopropylbenzene. The product mixture is cooled to precipitate essentially pure solid 1,2,4,5-tetraisopropylbenzene, which is then separated from the remaining liquid and transalkylated with benzene, cumene or diisopropylbenzene in the presence of the same clay to yield 1,3,5-triisopropylbenzene. Disadvantageously, this process produces large quantities of 1,2,4,5-tetraisopropylbenzene which must be transalkylated back to the more valuable 1,3,5-trialkyl compound.

In view of the above, there remains a need to recover the commercial value of isomeric mixtures of dialkyl- and trialkylbenzenes cheaply and efficiently. Moreover, there remains a need for an effective process of separating 1,3,5-trialkylbenzene from mixtures of the same and at least one of 1,2,4- and/or 1,2,3-trialkylbenzenes.

SUMMARY OF THE INVENTION

In one aspect this invention is a process of recovering monoalkylbenzene and pure 1,3,5-trialkylbenzene from an isomeric mixture of trialkyl- and dialkylbenzenes. The process comprises a transalkylation step and a subsequent separation of the transalkylation product mixture.

The transalkylation step comprises contacting a monocyclic aromatic compound with a transalkylating mixture containing at least one isomer of dialkylbenzene and at least one isomer of trialkylbenzene, wherein the alkyl groups each independently contain from one to about five carbon atoms. The contacting occurs in the presence of an acidic mordenite zeolite catalyst under reaction conditions such that a transalkylation product mixture is obtained containing monoalkylbenzene, 1,3,5-trialkylbenzene, residual amounts of 1,2,4- and/or 1,2,3-trialkylbenzenes, and optionally unreacted dialkylbenzenes. The catalyst is characterized by a $SiO_2/Al_2O_3$ molar ratio of at least about 30:1 and a crystalline structure having a Symmetry Index of at least about 1.0, as determined by X-ray diffraction. The catalyst of this process exhibits long life and is simply reactivated by a burn-off of carbonaceous deposits. More specifically, the catalyst shows essentially no deactivation up to at least about 500 hours of use.

The separation step comprises two parts. The first is the separation of monoalkylbenzene and any unreacted dialkylbenzene from the above-identified transalkylation product mixture. Such a separation yields commercially valuable monoalkylbenzene. Also recovered is unreacted dialkylbenzene, which can be recycled to the transalkylation reactor. Left behind as heavies are the trialkylbenzenes. The second separation step comprises the separation of pure 1,3,5-trialkylbenzene from a mixture of the same and 1,2,4- and/or 1,2,3-trialkylbenzenes. Specifically, 1,3,5-trialkylbenzene and residual amounts of 1,2,4- and/or 1,2,3-trialkylbenzenes are contacted with a zeolite Y aluminosilicate having a $SiO_2/Al_2O_3$ molar ratio of at least about 50:1 under conditions such that the 1,2,4- and/or 1,2,3-isomers are selectively adsorbed by the zeolite while the 1,3,5-isomer is not significantly adsorbed. In this manner an essentially pure fraction of 1,3,5-trialkylbenzene isomer is obtained.

The above-identified process of this invention is useful in up-grading the value of an isomeric mixture of dialkyl- and trialkylbenzenes. Valuable monoalkylbenzenes, such as cumene and ethylbenzene, are obtained. Moreover, 1,2,3- and 1,2,4-trialkylbenzenes may be converted via isomerization to more valuable 1,3,5-trialkylbenzene which is essentially unchanged under the process conditions and isolable in pure form. 1,3,5-trialkylbenzenes are useful as high temperature solvents and as starting materials for the synthesis of agricultural chemicals and K-resins.

As shown in related co-pending U.S. patent application Ser. No. 455,677, filed Dec. 22, 1989, the transalkylation process which is the first step in the overall process of this invention exhibits significant advantages over present day commercial transalkylation processes. Ethylbenzene and cumene, for example, are typically manufactured in a liquid or gas phase alkylation utilizing Friedel-Crafts catalysts, such as aluminum chloride. Disadvantageously, these processes require handling large quantities of aluminum chloride, designing corrosion resistant equipment, and disposing of a waste alumina and salt stream. In contrast, the process of this invention can be employed to transalkylate benzene with diethylbenzene or diisopropylbenzene to ethylbenzene or cumene, respectively, thereby advantageously eliminating the need for aluminum chloride, special corrosion resistant equipment and disposal of a metal oxide and salt waste stream. More advantageously, under the conditions of this process benzene is transalkylated to cumene having a low bromine index which correlates with a desirably low level of unsaturates. Even more advantageously, the process of this invention produces cumene which is nearly free of n-propylbenzene, o-diisopropylbenzene, butylbenzene and ethylbenzenes. As a further advantage, under the conditions of this process benzene can be transalkylated to ethylbenzene which is essentially free of xylenes. In contrast, the well-known Mobil-Badger process for manufacturing ethylbenzene produces large amounts of xylenes which are difficult to separate from ethylbenzene. In addition, the catalyst employed in this invention is active at temperatures lower than those typically employed in the Mobil-Badger process. In another advantage of this invention, the ortho, meta and para dialkylated benzenes transalkylate benzene at different rates with the para isomer reacting the fastest. These differences in reactivity establish the sensitive shape selective properties of the catalyst employed in the process of this invention, which properties may be exploited to accommodate shifting market demands.

Surprisingly, the catalyst employed in the transalkylation step in the process of this invention possesses a long lifetime and an unexpectedly low rate of deactivation. For this reason the catalyst of the invention is suitable for commercial application in any of the above-identified transalkylation processes.

Cumene produced by the practice of this invention is useful in the production of phenol. Ethylbenzene produced is useful in the production of styrene.

In a related aspect this invention is a process of separating 1,3,5-trialkylbenzene from a mixture of the same and 1,2,4- and/or 1,2,3-trialkylbenzene. The process comprises (a) contacting a mixture of 1,3,5-trialkylbenzene and at least one of 1,2,4- and 1,2,3-trialkylbenzene with a Zeolite Y adsorbent having a $SiO_2/Al_2O_3$ molar ratio of at least about 50 under conditions such that the 1,2,4- and/or 1,2,3-trialkylbenzene is selectively adsorbed, while 1,3,5-trialkylbenzene is not significantly adsorbed, (b) collecting the 1,3,5-trialkylbenzene in essentially pure form, and (c) modifying the conditions of the adsorbent bed such that the 1,2,4- and/or 1,2,3-trialkylbenzene is desorbed.

The utility of pure 1,3,5-trialkylbenzene is noted before.

DETAILED DESCRIPTION OF THE INVENTION

Any monocyclic aromatic compound can be transalkylated by the process of this invention. The aromatic compound is preferably benzene or substituted benzene. More preferably, the substituted benzene has a substituent other than an alkyl group. Non-limiting examples of substituted benzenes which may be transalkylated by the process of this invention include phenol, aniline, chlorobenzene and dichlorobenzene. Most preferably, the aromatic compound is benzene.

A transalkylating mixture is required for this process, and typically the mixture comprises at least one isomer of a dialkylbenzene and at least one isomer of a trialkylbenzene. Suitable mixtures include the ortho, meta and para isomers of dialkylbenzenes in combination with 1,3,5- and/or 1,2,4-trialkylbenzene isomers. 1,2,3-Trialkylbenzene may also be employed, although it is not readily available from standard alkylation methods. The alkyl group on the tri- and dialkyl isomers each independently contains from one to about five carbon atoms, preferably, from two to four carbon atoms, and more preferably, three carbon atoms.

Several non-limiting examples of dialkylbenzenes include dimethylbenzenes, diethylbenzenes, di-n-propylbenzenes, di-isopropylbenzenes, di-n-butylbenzenes, di-sec-butylbenzenes, di-t-butylbenzenes, di-pentylbenzenes, as well as ethylpropylbenzenes, ethylbutylbenzenes, and propylbutylbenzenes. Several non-limiting examples of trialkylbenzenes include the various isomers of trimethylbenzene, triethylbenzene, tri-n-propylbenzene, tri-isopropylbenzene, tri-n-butylbenzene, tri-sec-butylbenzene, and tri-t-butylbenzene, and the various tripentylbenzenes, as well as methyldiethylbenzenes, methyldipropylbenzenes, ethyldipropylbenzenes, dimethylpropylbenzenes, diethylpropylbenzenes, diethylbutylbenzenes, dipropylbutylbenzenes, and dipropylpentylbenzenes. In a preferred embodiment, benzene is transalkylated by a mixture of o-, m-, and p-diisopropylbenzenes in the presence of triisopropylbenzenes to produce cumene. In another preferred embodiment, benzene is transalkylated by a mixture of o-, m-, and p-diethylbenzenes in the presence of triethylbenzenes to produce ethylbenzene.

The alkylaromatic mixtures, described hereinabove, may be obtained by any synthetic method, preferably however, by the direct alkylation of benzene in the presence of catalysts, such as phosphoric acid or acidic zeolites. For example, mixtures of triisopropylbenzenes and diisopropylbenzenes are obtained as "heavies" in the alkylation of benzene with propylene to form cumene. Similarly, mixtures of triethylbenzenes and diethylbenzenes are obtained as "heavies" in the alkylation of benzene with ethylene to form ethylbenzene.

The concentration of trialkylbenzenes in the alkylaromatic mixture can vary over a wide range, for example, from about 5 weight percent to about 75 weight percent, preferably from about 5 weight percent to about 20 weight percent.

The monocyclic aromatic compound and transalkylating mixture may be contacted neat in a liquid state or dissolved in a suitable solvent. Preferably, the aromatic compounds are used in a neat liquid state. If a solvent is employed, any inert solvent which solubilizes the aromatic compounds and does not hinder the transalkylation reaction may be used. The preferred solvent is decalin.

The transalkylation catalyst useful in the practice of this invention is an acidic mordenite zeolite having a silica/alumina molar ratio of at least 30:1, a Symmetry Index (SI) as defined hereinafter of at least about 1.0, and a porosity such that the total pore volume is in the range from about 0.18 cc/g to about 0.45 cc/g, and the ratio of the combined meso- and macropore volume to the total pore volume is in the range from about 0.25 to about 0.75. For the purposes of this invention, a micropore has a radius in the range of about 3 angstrom units (Å) to 10 Å radius in the range of 10 Å to 100 Å, and a macropore has a radius in the range of 100 Å to 1000 Å.

The catalyst useful in this invention is prepared by a process which comprises contacting with strong acid an acidic mordenite zeolite having a silica/alumina molar ratio less than 30:1 and a crystalline structure which is determined by X-ray diffraction to possess a Symmetry Index (SI) of from about 0.5 to about 1.3 under conditions sufficient to remove an amount of alumina sufficient to provide a silica/alumina molar ratio of at least 30:1. The process of preparing the catalyst is described in detail hereinbelow.

The catalyst of the invention is an acid-modified zeolite with interconnecting twelve-ring and eight-ring channels. Zeolites have framework structures that are formally constructed from silicate and aluminate tetrahedra that share vertices. The tetrahedra may be linked to form pores or channels. The size of the pores is determined by the number of tetrahedra in the ring. Twelve-ring zeolites contain rings formed from twelve tetrahedra. Eight-ring zeolites contain rings formed from eight tetrahedra. The zeolites of this invention contain interconnecting twelve-ring and eight-ring channels. Examples of the zeolites suitable for use in this invention are mordenite, offretite and gmelinite. Mordenite-like zeolites, such as ECR-1 which is described in U.S. Pat. No. 4,657,748, and intergrowths of mordenite with other zeolites are also suitable catalysts, as are zeolites having a one-dimensional pore system with twelve-ring channels, such as type L or related zeolites. Preferably the catalyst is an acidic mordenite zeolite.

Natural mordenite is an aluminosilicate whose typical unit cell contents are assigned the formula $Na_8[(AlO_2)_8\cdot(SiO_2)_{40}\cdot 24 H_2O]$. Mordenite is the most siliceous natural zeolite with a silicon/aluminum mole ratio (Si/Al) of about 5/1. The dimensions of the twelve-ring pores are about $6.7 \times 7.0$ Å: the dimensions of the eight-ring pores are about $2.9 \times 5.7$ Å. The structure and properties of mordenite zeolite are described in *Zeolite Molecular Sieves*, by Donald W. Breck (John Wiley & Sons, 1974), at pages 122-124 and 62-163, which is incorporated herein by reference.

The catalyst of this invention is prepared from a mordenite zeolite typically containing cations of the alkali or alkaline earth metals, or alternatively ammonium ions. Depending upon the source of the raw materials employed in preparing the starting mordenite, the latter may contain varying amounts of metal ions other than the above-identified ones. Mordenites prepared from clays, for example, may contain significant amounts of iron, lesser amounts of cobalt, copper and nickel, and even lesser amounts of other transition and rare earth elements. Mordenites prepared from fumed silica, however, may contain only trace amounts of these extraneous metals, since fumed silica is generally quite pure. Preferably, the catalyst of the invention is prepared from a sodium mordenite zeolite: even more preferably, from a sodium mordenite having a Symmetry Index less than about 1.0. The Symmetry Index is a dimensionless number obtained from the X-ray diffraction pattern of the sodium mordenite being measured in the hydrated form. Standard techniques are employed to obtain the X-ray data. The radiation is the $K\alpha_1$ line of copper, and a Philips Electronics spectrometer is used. The mordenite zeolites exhibit an X-ray diffraction pattern whose diffraction peaks have d-spacings corresponding to those of crystalline mordenites as reported by J. D. Sherman and J. M. Bennett in "Framework Structures Related to the Zeolite Mordenite," *Molecular Sieves*: J. W. Meier and J. B. Uytterhoeven, eds., *Advances in Chemistry Series*, 121, 1973, pp. 52-65. The Symmetry Index is defined as the sum of the peak heights of the 111] (13.45, $2\theta$) and 241] (23.17 $2\theta$) reflections divided by the peak height of the [350] (26.25 $2\theta$) reflection. Preferably, the Symmetry Index of the sodium mordenite ranges from about 0.5 to about 1.3. More preferably, the Symmetry Index of the sodium mordenite ranges from about 0.7 to about 1.3.

Four ordered crystalline structures have been proposed to describe the X-ray diffraction data available for natural and synthetic mordenite zeolites. (J. D. Sherman and J. M. Bennett, op.cit., p. 53.) The symmetries of these four structures are Cmcm, Cmmm, Imcm, and Immm as these terms are defined by N. F. M. Henry and K. Lonsdale in *International Tables for X-ray Crystallography*, 3rd Ed., Volume 1, Kynoch Press (1969). X-ray diffraction data indicate that mordenites are either physical admixtures or intergrowths of the Cmmm, Imcm, or Immm structures with the Cmcm structure. Thus, mordenites can be generally described as having a crystalline structure comprising a matrix of Cmcm symmetry having dispersed therein domains of Cmmm, Imcm, or Immm symmetry, or mixtures thereof. Preferably, the mordenite of this invention has a crystalline structure comprising a matrix of Cmcm symmetry having dispersed therein domains of Cmmm symmetry. The Symmetry Index is related to the symmetries of the crystals present in the mordenite sample. A Symmetry Index in the range from about 0.5 to about 1.3 provides a suitable sodium mordenite as starting material for the process of this invention.

The crystallite size of the original sodium mordenite may be any size which yields a catalyst effective for the transalkylation of benzene or substituted benzene. Preferably, the crystallite size is effective for the preparation of cumene having a low bromine index and low impurity levels. Typically, the crystallite size may be in the range from about 500 Å to about 5000 Å. Preferably, the crystallite size is in the range from about 500 Å to about 2000 Å; more preferably, from about 800 Å to about 1500 Å. Generally, the crystallites form aggregates which may be used as such or bound into larger particles for the process of this invention. For example, extrudate can be made for a packed-bed reactor by compressing the aggregates into binderless particles of suitable sizes. Alternatively, the extrudate can be made via use of binders well-known to those in the art. Non-limiting examples of binders include alumina and silica, with silica being the preferred binder. Typically, the concentration of binder ranges from about 0 to about 90 weight percent of the bound catalyst composition, preferably, from about 5 to about 70 weight percent of the bound catalyst composition, more preferably, from about 5 to about 40 weight percent of the bound catalyst composition.

The original sodium mordenite zeolite described hereinabove, or its equivalent, is treated to obtain the catalyst of the invention for use in the transalkylation process. The treatment involves contacting the mordenite with acid. In one preferred embodiment, the treatment involves contacting the mordenite with acid, calcining the acid-treated mordenite, and further contacting the calcined mordenite with strong acid. In an alternative preferred embodiment, the catalyst is prepared without being calcined.

The initial acid treatment serves to remove most of the sodium ions, or their equivalents, from the original mordenite. The treatment may remove a portion of the aluminum ions as well. Inorganic acids and organic acids are suitable compounds from which the hydrogen ions are obtained for the acid treatment. Examples of such acids are hydrochloric acid, hydrobromic acid, sulfuric acid, phosphoric acid, nitric acid, acetic acid, oxalic acid, and the like. Inorganic acids are the preferred source of hydrogen ions; with hydrochloric, nitric and phosphoric acids being more preferred and hydrochloric acid being most preferred. An equally acceptable initial treatment involves ion exchange with ammonium salts, such as ammonium chloride. By this method the sodium ions, or their equivalents, are removed, but the aluminum ions are not displaced. On heating the ammonium exchanged mordenite, ammonia is given off and the mordenite is converted to the acid form.

Typically, in the initial acid treatment the original sodium mordenite is slurried with an aqueous solution of the acid. The acid solution may have any concentration, providing the catalyst obtained possesses the properties and activity of the catalyst of this invention, these being described hereinafter. Preferably, the concentration of the aqueous acid solution is in the range from about 0.01N to about 6N; more preferably in the range from about 0.5N to about 3.0N. The relative quantities of aqueous acid solution to mordenite solid which are employed may vary. Typically, the ratio is less than about 15 cc acid solution per gram mordenite solid. Preferably, the ratio is in the range from about 5 cc acid solution per gram mordenite solid to about 10 cc acid solution per gram mordenite solid. The temperature and the duration of the contact of the mordenite with the acid solution may also vary. Preferably, the mordenite is contacted with the acid at a temperature in the range from about 10° C. to about 100° C. Generally, the contact time between the acid solution and the mordenite may vary from about 5 minutes to about several hours. It is important that there be sufficient time for the acid solution to contact all of the mordenite particles. Preferably, the contact time is from about 5 minutes to about 60 minutes. The acid extraction, as described herein, may be repeated if desired. Afterwards, the mordenite is washed in water one or more times in order to rinse away soluble species from the mordenite. Preferably, the water wash is carried out at ambient temperature. Optionally, subsequent to the water wash the mordenite is dried in air at a temperature in the range from about 20° C. to about 150° C.

In one treatment, following the exchange with acid and drying in air, the acidic mordenite zeolite is calcined in air or heated in an inert atmosphere, such as nitrogen. It is believed that this heat treatment dislocates a portion of the aluminum from the zeolite framework; however, such a theory should not be taken as limiting of the scope of the invention. Typically, the temperature of the calcination or heating is in the range from about 300° C. to about 800° C. Preferably, the temperature is in the range from about 500° C. to about 750° C. More preferably, the temperature is from about 650° C. to about 750° C.

After calcining the acid-treated mordenite described hereinabove, the mordenite is subjected to an additional acid treatment for the purpose of further dealumination. The second acid treatment comprises contacting the calcined mordenite with a strong acid under conditions sufficient to produce the acidic mordenite catalyst of this invention. For the purposes of this invention a "strong" acid is defined as an acid which reacts essentially completely with the solvent to give the conjugate acid of the solvent. For example, if gaseous hydrogen chloride is dissolved in water, the acid-base reaction is complete to give the conjugate acid $H_3O+$ and $Cl-$. Preferably, the strong acid is an inorganic acid. More preferably, the strong acid is nitric acid, hydrochloric acid, or sulfuric acid. Most preferably, the strong acid is nitric acid. The concentration of the strong acid will vary depending on the acid selected. In general, the acid is employed in an aqueous solution of any concentration which provides for the extraction of aluminum from the calcined acidic mordenite, as described hereinafter. With nitric acid, for example, the concentration of the acid in the aqueous solution is preferably in the range from about 2N to about 15N. More preferably, the concentration of the acid is in the range from about 4N to about 12N. Most preferably, the concentration of the acid is in the range from about 6N to about 8N. The aqueous acid solution and the calcined mordenite are contacted in any ratio that provides the catalyst of the invention. Preferably, the ratio of aqueous acid solution to mordenite is in the range from about 3 cc acid solution per gram mordenite to about 10 cc acid solution per gram mordenite. More preferably, the ratio is about 5 cc acid solution per gram mordenite. The temperature and the duration of the contact may vary depending on the acid selected. Preferably, the mordenite is contacted with the acid solution at a temperature in the range from about ambient temperature taken as 22° C. to about 220° C. More preferably, the mordenite and the acid are contacted at a temperature which allows for boiling of the aqueous acid under atmospheric conditions. Preferably, the duration of the contact is from about 1 hour to about 6 hours: more preferably, from about 1 hour to about 3 hours: most preferably, for about 2 hours. When the contacting with strong acid is complete, the mordenite is filtered and washed repeatedly with water until the washings are acid-free. Preferably, the washed mordenite is heat treated and contacted with strong acid more than once. Lastly, the washed acidic mordenite zeolite is dried for several hours at a temperature in the range from about 100° C. to about 150° C. to remove physically adsorbed water. The dried acidic mordenite is activated by heating for about 2 hours at a temperature in the range from about 300° C. to about 700° C. This activation may drive off more strongly bound water and any residual adsorbates.

In an alternative embodiment, the original sodium mordenite is treated with acid and retreated with strong acid without the intermediate calcination step.

After the original sodium mordenite is treated with acid, optionally calcined, and retreated with strong acid according to the process of this invention, an acidic mordenite catalyst is obtained which is capable of transalkylating dialkylbenzenes selectively to monoalkylbenzenes in the presence of trialkylbenzenes. Moreover, benzene can be transalkylated to cumene or ethylbenzene having low levels of impurities and a low bromine index. 1,2,4- and 1,2,3-trialkylbenzenes may be isomerized to 1,3,5-trialkylbenzene, which is essentially unchanged under the process conditions. This catalyst exhibits special characteristics by which it may be identified, specifically, the silica/alumina molar ratio, and the Symmetry Index and porosity as defined hereinafter.

An additional characteristic of the catalyst is its minimal deactivation in the transalkylation process of the present invention. Surprisingly, the catalyst remains active for long periods of use even in the presence of trialkylbenzenes, which are known in the prior art to deactivate prior art transalkylation catalysts. By remaining active, it is meant that the catalyst of this invention retains at least about 60, more preferably about 75, and most preferably about 90 percent of its activity for a period of at least about 500 hours of use, more preferably for at least about 750 hours of use, and most preferably for at least about 900 hours of use. The catalyst preferably remains active significantly longer than 900 hours of use.

In the transalkylation process of the present invention, the catalyst, should it show any deactivation, may be regenerated by a burn-off of carbonaceous deposits. This may be effected by passing an oxygen-containing gas over the catalyst at a temperature of 400°-700° C.

As a result of the acid extractions, the silica/alumina molar ratio ($SiO_2/Al_2O_3$) of the acidic mordenite catalyst is increased over that of the original sodium mordenite. Specifically, the acid-treated mordenite catalyst has a silica/alumina molar ratio of at least 30:1. Preferably, the silica/alumina molar ratio ranges from about 50:1 to about 500:1, more preferably, from about 50:1 to about 300:1, most preferably from about 60:1 to about 100:1.

As a further result of the acid extractions and optional calcination, the Symmetry Index of the mordenite catalyst is increased over that of the original mordenite. The Symmetry Index is as defined hereinbefore. Since the Symmetry Index is derived from X-ray data, the Index is related to the proportion of Cmcm, and Cmmm, Imcm, or Immm symmetries present in the catalyst. The increase in the Symmetry Index is indicative of the enrichment of the catalyst in the Cmcm component. For alkylations, a Symmetry Index of at least about 1 results in catalysts showing minimal deactivation that are capable of achieving high yields of monoalkylated benzenes. Preferably, the Symmetry Index ranges from about 1 to about 2.

A third property of the acidic mordenite catalyst, by which it is identified, is the porosity. All zeolites possess pores which form as a natural consequence of zeolite crystal growth. New pores or modifications of existing pores can occur on treating the zeolites, for example, with heat or acid as in the process of this invention.

Typically, pores are classified into micropores, mesopores and macropores. For the purposes of this invention a micropore is defined as having a radius in the range from about 3 Angstrom units (3 Å) to 10 Å. Likewise, a mesopore is defined as having a radius in the range from 10 Å to 100 Å, while a macropore is defined as having a radius from 100 Å to 1000 Å. After calcination and strong acid treatment, the acidic mordenite catalyst of this invention possesses micro-, meso- and macropores. The porosity of the catalyst may be distinguished by the total pore volume defined as the sum of the volumes of the micro-, meso-, and macropores per gram catalyst. A catalyst of this invention has a total pore volume sufficient to provide a high yield of the desired monoalkylated benzene with low levels of impurities. Preferably, the total pore volume is in the range from about 0.18 cc/g to about 0.45 cc/g. The porosity may be further distinguished by the relative distribution of meso- and macropores, as found in the ratio of the combined meso- and macropore volume to the total pore volume. A catalyst of this invention has a ratio of combined meso- and macropore volume to total pore volume sufficient to provide a high yield of the desired alkylated aromatics with low levels of impurities. Preferably, the ratio of the combined meso- and macropore volume to total pore volume is in the range from about 0.25 to about 0.75.

The measurement of the porosity, described hereinabove, is derived from surface area and pore volume measurements of mordenite powders obtained on any suitable instrument, such as a Quantachrome Digisorb-6 unit, using nitrogen as the adsorbate at the boiling point of nitrogen, 77 K. The total pore volume (VT) is derived from the amount of nitrogen adsorbed at a relative pressure close to unity. It is accepted that this volume constitutes pores of less than 1000 Å in radius. As stated earlier, for the purposes of this invention pores with radius of 10 Å or less are called micropores. Pores with radius from 10 Å to 100 Å are called mesopores, and pores with radius from 100 Å to 1000 Å are called macropores. Pores with radius in the 10 Å to 1000 Å range are known in the literature as "transitional pores." The micropore volume ($V_m$) in the presence of "transitional pores" is obtained by the t-method. The difference between the total pore volume and the micropore volume is the transitional pore volume, ($V_t = V_T - V_m$). The cumulative pore distribution in the transitional pore range is used to calculate the relative volume contributions of mesopores and macropores. For example, the mesopore volume is calculated by multiplying the transitional pore volume by the fraction of the cumulative pore volume from 10 Å to 100 Å, ($V_{me} = V_t f_{me}$). The macropore volume is then simply obtained by subtracting the mesopore volume from the transitional volume, ($V_{ma} = V_t - V_{me}$). This approach ensures that the equation $V_T = V_m + V_{me} + V_{ma}$ is satisfied. The adsorption isotherms obtained for the mordenite catalysts of this invention are of Type I, which are described by the Langmuir equation. The Langmuir surface area is obtained from such equation. The methods used to obtain surface areas and pore volumes are described by S. Lowell in *Introduction to Powder Surface Area* (John Wiley and Sons, 1979), or in the manuals provided with the Digisorb-6 instrument made by the Quantachrome Corporation.

The acidic mordenite catalyst, identified hereinabove, is capable of adsorbing biphenyl into the intracrystalline pore system, and conversely desorbing biphenyl. Biphenyl adsorption is effected by exposing the acidic mordenite to biphenyl vapors at 100° C. for a time sufficient to obtain near constant weight. Preferably, the adsorption capacity of the acidic mordenite for biphenyl is about 5 weight percent. More preferably, the capacity is about 10 weight percent. Biphenyl desorption is effected by heating the mordenite-biphenyl sample in a dynamic helium atmosphere from 25° C. to about 1000° C. at a heating rate of about 10° C./minute. The desorption of biphenyl may be followed experimentally by thermal gravimetric analysis combined with gas phase chromatography and mass spectrometry (TGA-GC-MS). It is found that weakly adsorbed biphenyl produces a weight loss at temperatures below about 300° C.: whereas, strongly adsorbed biphenyl produces a weight loss at temperatures from about 300° C. to as high as 1000° C. The amount of strongly adsorbed biphenyl is estimated by subtracting the amount of weakly adsorbed biphenyl from the total amount of biphenyl desorbed from the sample. A fully treated mordenite catalyst of this invention exhibits a sharp weight loss at temperatures below about 300° C., and little or no weight loss from 300° C. to 1000° C. In contrast, acid-exchanged mordenite exhibits a sharp weight loss at temperatures below about 300° C., and a second weight loss starting at about 300° C. and extending to 1000° C. It is believed that the weakly adsorbed biphenyl is located in sites from which there is relatively easy exit: whereas the strongly adsorbed biphenyl is located in sites from which there is relatively difficult exit. Thus, the acidic mordenite catalyst of this invention provides easy access and egress to adsorbed biphenyl. Such a theory, however, should not be construed to be binding or limiting of the scope of the invention.

As a further preferred characteristic, the acidic mordenite zeolite of this invention is not treated with metals or metal ions. Thus, the acidic mordenite is essentially free of metals with the exception of those present in the starting zeolite which occur in low amounts and which may not be removed by acid treatment. The term "essentially free" means that the concentration of any metal or metal ion is less than about 5 weight percent, preferably less than about 3 weight percent, and more preferably, less than about 1 weight percent. This exclusion relates to metals in their reduced zerovalent form as well their oxides, both of which could be deposited onto the mordenite by one skilled in the art. The exclusion also relates to ionic forms of the metals which can be ion-exchanged into the mordenite by one skilled in the art. Non-limiting examples of metals which preferably are not added to the acidic mordenite include those selected from Groups IIIA, IVA, VA, VIA, VIIA, VIII, IB, IIB and the rare earth metals of the Periodic Table, as well as gallium, tin, lead, antimony, bismouth and thorium. More preferred metals which are to be excluded include the metals of Group VIII, such as iron, cobalt, nickel, palladium, platinum, rhodium, ruthenium and iridium: the rare earth metals including lanthanum, cerium, praeseodymium, neodymium, samarium, gadolinium, and dysprosium; Group IB metals including copper, silver and gold: and Group VIA metals including tungsten, molybdenum and chromium. As noted hereinbefore, Group IA and IIA metal ions may be present in trace amounts.

The catalyst useful in the process of this invention is not sensitive to the small amounts of water which may be present in benzene or substituted benzene. Accordingly, the benzene or substituted benzene reactant does not have to undergo a drying treatment, which is another advantage of the present process.

The ratio of benzene or substituted benzene to catalyst may be any weight ratio which produces the desired monoalkylated benzene with a relatively high selectivity and low level of impurities. Preferred ratios will also be dependent on the reactor configuration. For example, in batch reactors, the weight ratio of benzene or substituted benzene to catalyst is preferably in the range from about 0.1:1 to about 2000:1. More preferably, the weight ratio is in the range from about 10:1 to about 500:1. Most preferably, the ratio is in the range from about 50:1 to about 100:1. Below the preferred lower limit of 0.1:1, the productivity will be very low. Above the preferred upper limit of 2000:1, the conversion of the aromatic compound may be low. In a continuous mode of operation the weight hourly space velocity (WHSV) of the overall feed with respect to catalyst is preferably in the range from about 0.1 to about 100. More preferably, the WHSV is in the range from about 0.1 to 20.

The molar ratio of the total benzene groups in benzene or substituted benzene and in dialkylated benzene or dialkylated substituted benzene to the total alkyl groups on the dialkylated benzene or dialkylated substituted benzene may vary depending on the identity of the alkyl substituent, type of reaction such as batch or continuous, and reaction conditions such as temperature, pressure and weight hourly space velocity (WHSV). Typically, this molar ratio is at least about 1.5:1. In case of a lower ratio the selectivity to the monoalkylated product is decreased. More preferably, the molar ratio is from about 2:1 to about 4:1. As is recognized by one skilled in the art, when different reactor configurations are used, different ratios of reactants may be preferred. Since trialkylbenzenes exhibit low transalkylation reactivity, if any, in the process of this invention, their presence does not affect the ratio of benzene to dialkylbenzenes.

The benzene or substituted benzene and transalkylating mixture may be introduced into the reactor or reaction zone all at once or on demand or by multiple injection as in the case of a batch reactor, or as separate feeds or as combined feeds as in the case of a continuous transalkylation process. Further, in the case of a continuous transalkylation process, either the benzene or substituted benzene and the transalkylating mixture may be introduced to the reactor or reaction zone as a single feedstream or split into a plurality of feedstreams which are introduced into the reactor at different locations. In the transalkylation process of the present invention, preferably a plurality of catalyst-containing reaction zones in fluid connection in series is used, wherein the whole of the benzene or substituted benzene is delivered to a first reaction zone, and a series of fractions of transalkylating mixture are delivered respectively to the first reaction zone and between each pair of contiguous reaction zones. Operating the process in this way increases the selectivity towards the monoalkylated product compared to supplying the whole of the transalkylating agent to the first transalkylation reaction zone.

The contacting of benzene or substituted benzene with the transalkylating mixture containing dialkyl- and trialkylbenzenes may occur in a reactor of any configuration. Batch-type and continuous reactors, such as fixed bed, slurry bed, fluidized bed, catalytic distillation, or countercurrent reactors, are suitable configurations for the contact. Preferably, the reactor is a continuous flow reactor.

In a continuous transalkylation of the present invention, the reaction is preferably carried out under conditions sufficient to keep the reaction mixture in the liquid phase. Most preferably, the reactor is operated in a substantially full liquid mode. The benzene or substituted benzene may be in the molten, liquid form or in solution. Usually, the transalkylating mixture is in the molten, liquid form, and may be premixed with the benzene reactant. The catalyst may be used in various forms, such as a fixed bed, moving bed, fluidized bed, in suspension in the liquid reaction mixture, or in a reactive distillation column.

The contacting of the reactants in the presence of the catalyst may occur at any temperature or pressure which will selectively transalkylate the benzene reactant with dialkylbenzene to form monoalkylbenzene, while leaving the 1,3,5-trialkylbenzene essentially unchanged. Typically, the temperature is in the range from about 140° C. to about 300° C. These temperatures are relatively mild for zeolite catalyzed type transalkylation processes. In the preferred production of cumene from benzene and diisopropylbenzene, the temperature is preferably in the range from about 140° C. to about 250° C. In another preferred production of ethylbenzene from benzene and diethylbenzene, the temperature is preferably in the range from about 200° C. to about 300° C. Below the preferred lower limit of 140° C. the reaction proceeds slowly. Above the preferred upper limit of 300° C., the impurity level increases.

The pressure in the reactor may be any pressure sufficient to keep the reaction mixture as a liquid under reaction conditions. The required pressure will change depending on temperature and reactants employed. In batch reactors the pressure typically rises to the vapor pressure of the benzene reactant at the temperature of the reaction. Preferably the pressure is in the range from about 1 bar to about 200 bar. More preferably, the pressure is in the range from about 20 bar to about 100 bar.

The monocyclic aromatic compound (benzene) reactant, transalkylating mixture and catalyst are contacted for a time sufficient to convert the monocyclic aromatic compound to monoalkylated product without forming too many impurities. Generally, the contact time will depend on other reaction conditions, such as temperature, pressure and reagent/catalyst ratios. In the production of cumene from benzene and diisopropylbenzene in a typical stirred batch reactor with a benzene:-catalyst ratio of about 50:1, at 150° C., and a stirring rate of 2000 rpm, for example, the reaction time is preferably in the range from about 0.1 hour to about 10 hours. More preferably, the reaction time is in the range from about 1 hour to about 4 hours.

Following the transalkylation of the benzene or substituted benzene, the product mixture contains monoalkylated product, essentially the original quantity of trialkylbenzene, and optionally unreacted dialkylbenzene. For example, in the transalkylation of benzene with an isomeric mixture of di- and triisopropylbenzenes the product mixture contains cumene, residual diisopropylbenzne, and essentially the original quantity of triisopropylbenzene, generally as the 1,3,5-isomer with much lesser amounts of the 1,2,4-isomer. Under the transalkylation conditions of this invention about 90 percent or more of the 1,2,4- and/or 1,2,3-isomers usually isomerize to the 1,3,5- isomer. Thus, 1,3,5-trialkylbenzene is the predominant trialkyl isomer in the product.

Monoalkylbenzene is separated from the transalkylation product mixture by methods known in the art. The simplest method comprises fractional distillation which yields a monoalkyl fraction and a dialkyl fraction and a trialkyl "heavies" fraction. In the preferred transalkylation of benzene with a mixture of di- and triisopropylbenzenes, the distillation readily yields a cumene fraction, an unreacted diisopropylbenzene fraction which may be recycled to the transalkylation reactor, and a "heavies" fraction comprising essentially 1,3,5-triisopropylbenzene.

For the purposes of this invention, the term "conversion" refers to the mole percent of dialkylbenzene which reacts with benzene to form monoalkylated product. Typically, in a batch reaction to produce cumene from benzene and diisopropylbenzene, the conversion achieved in the practice of this invention is in the range from about 10 to about 75 mole percent. Below 10 percent conversion the separation of diisopropylbenzene from triisopropylbenzene is not efficient. Above 75 percent conversion, unacceptable levels of unwanted by-products, particularly n-propylbenzene, may form.

For the purposes of this invention, the term "dialkylbenzene selectivity" refers to the mole percent of reacted dialkylbenzene which is converted to monoalkylated product, such as cumene or ethylbenzene. Smaller amounts of various by-products such as n-propylbenzene, butylbenzenes and xylenes are also formed. Typically, the dialkylbenzene selectivity to cumene or ethylbenzene ranges from about 70 mole percent to more than 99 mole percent.

Likewise, the term "benzene selectivity" refers to the mole percent of reacted benzene which is converted to desired product such as cumene or ethylbenzene. Smaller amounts of various by-products, such as n-propylbenzene, butylbenzenes and xylenes are also formed. Typically, the benzene selectivity to cumene or ethylbenzene ranges from about 70 mole percent to more than 99 mole percent.

The concept of simultaneous high conversion and high selectivity to desired product may be expressed conveniently in terms of yield. For the purposes of the present invention, the term "yield" refers to the numerical product of conversion and selectivity. For example, a process to produce cumene according to the present invention operating at a benzene conversion of 15 percent and a selectivity to cumene of 85 percent would have a yield of cumene of 12.75 percent, which is the numerical product of 15 percent and 85 percent. Typically, the yield of cumene or ethylbenzene achieved in the process of this invention, not considering any recycle or reactants, is at least about 10 mole percent and is preferably at least about 15 mole percent.

An additional factor that is important is the presence of various impurities in the product. Even very small amounts of certain impurities such as n-propylbenzene or propylene oligomers in the case of cumene, or xylenes in the case of ethylbenzene, create significant problems in various applications. Processes run under different conditions result in different levels of impurities. Thus, a particular advantage of the process of the present invention is the low impurity levels. In the case of cumene production, low levels of oligomers as indicated by low bromine index is also important. In cumene production, the bromine index is preferably no greater than about 100, more preferably no greater than about 50 and most preferably no greater than about 20. Cumene produced by the process of this invention preferably contains less than about 1000 parts per million (ppm) impurities, more preferably less than than 200 ppm. Ethylbenzene produced by the process of this invention has less than about 1000 ppm xylene impurities, more preferably less than about 500 ppm, most preferably less than about 100 ppm.

An additional characteristic of the cumene produced by the process of this invention is the amount of color in the product. The cumene produced by the practice of this invention is essentially colorless.

The trialkylbenzene obtained in the transalkylation process described hereinabove comprises the 1,3,5 isomer contaminated with residual amounts, typically less than about 5 percent, of the 1,2,4-isomer, and usually only trace amounts of the 1,2,3-isomer. The 1,2,4 and 1,2,3 isomers can be removed by passing the isomeric mixture through an adsorbent comprising zeolite Y aluminosilicate having a $SiO_2/Al_2O_3$ molar ratio of at least about 50:1 under conditions such that the 1,3,5-trialkylbenzene is not significantly adsorbed while the 1,2,4- and 1,2,3- isomers are significantly adsorbed by the zeolite. Under the separation process conditions 1,3,5-trialkylbenzene is obtained as an essentially pure compound.

Zeolite Y comprises a crystalline aluminosilicate having the unit cell composition:

$$Na_{56}(AlO_2)_{56}(SiO_2)_{136}]\cdot 250\ H_2O$$

and a three dimensional interconnected faujasite-type, cubic structure as defined by U.S. Pat. No. 3,130,007, incorporated herein by reference. This aluminosilicate is also described by Donald W. Breck in Zeolite Molecular Sieves, John Wiley & Sons, Inc., New York, 974, pp. 85, 92-95 and 177. In accordance with this invention, the zeolite Y is required to be dealuminized such that the $SiO_2/Al_2O_3$ molar ratio is at least about 0:1. Preferably, the $SiO_2/Al_2O_3$ molar ratio ranges from about 50:1 to about 1000:1; more preferably from about 250:1 to about 600:1. Dealuminized zeolite Y is commercially available.

The dealuminized zeolite Y adsorbent can be employed as binderless aggregates, or can be bound into aggregates or extrudate with binders, such as silica, kaolin, or alumina. Preferably, the adsorbent is prepared into extrudate with a binder of alumina.

The dealuminized zeolite Y adsorbent is employed usually in the form of a compact fixed bed which is alternately contacted with the trialkylbenzene feed mixture and desorbent materials. The feed mixture and desorbent materials can be applied in the liquid phase to the adsorbent, as in a typical liquid chromatography column. Alternatively, the feed mixture can be contacted in the gas phase with the solid adsorbent bed, and a raffinate stream containing the 1,3,5-trialkylbenzene isomer can be collected until at least one other trialkylbenzene isomer breaks through the adsorbent bed into the raffinate stream. At this point the feed stream is stopped, and the adsorbed trialkylbenzene isomers, predominantly 1,2,4-trialkylbenzene, are removed from the adsorbent bed by changing the temperature and/or pressure of the bed. This method is known in the art as the "temperature or pressure swing method" and is described by Ralph T. Yang in Gas Separation by Adsorption Process, Buttersworth, 1987, Chapters 6, 7, and 8, relevant portions of which are incorporated herein.

Optionally, a desorbent may be employed in the separation process of this invention. The function of the desorbent is to increase the rate of desorption of the adsorbed isomers. Preferably, a desorbent is employed. The desorbent may be any liquid or gas which is nonreactive with the zeolite Y adsorbent and trialkylbenzene isomers, and which aids in desorbing the isomers from the adsorbent bed. If the desorbent is a liquid, it is generally selected from the group consisting of alkanes or alkylaromatics having up to about 20 carbon atoms. Preferably, the liquid desorbent is p-diethylbenzene or n-hexane. If the desorbent is a gas, it is generally selected from the group consisting of helium, nitrogen, and steam. Preferably the gaseous desorbent is helium or nitrogen.

Any operative temperature is suitable for passing the feedstream and desorbent streams through the adsorbent, provided that the feedstream is in the liquid or gaseous state and not subject to decomposition. Preferably, the temperature for the process of this invention ranges from about room temperature to about 100° C. above the average boiling point of the trialkylbenzene isomeric mixture. More preferably, the temperature ranges from about room temperature to about the average boiling point of the trialkylbenzene.

Any operative pressure is suitable for passing the feedstream and desorbent streams through the adsorbents, provided that the feedstream is maintained in the liquid or gaseous state. The pressure will vary considerably depending upon the design and size of the adsorbent bed, the particle size of the adsorbent, the temperature of the bed, and whether the feedstream or the desorbent stream is being employed. Typically, the pressure will vary from subatmospheric to superatmospheric.

By passing the trialkylbenzene isomeric mixture through an adsorbent bed of zeolite Y, 1,3,5-trialkylbenzene is recovered in an essentially pure fraction. For the purposes of this invention the phrase "essentially pure" means a purity of at least about 99 weight percent. A preferred trialkylbenzene recovered in at least about 99 weight percent purity is 1,3,5-triisopropylbenzene.

After collection of the 1,3,5-isomer, the conditions of the adsorbent bed are varied such that the 1,2,4-, and if any, 1,2,3-trialkylbenzene isomers are desorbed and collected for recycle to the transalkylation reaction. The conditions for recovery of the 1,2,4-, and 1,2,3-isomers will vary depending upon the design of the adsorbent bed, and may include liquid or gaseous desorbents, and use of the pressure and temperature swing method.

ILLUSTRATIVE EMBODIMENTS

The following examples are given to illustrate the processes of this invention and should not be construed as limiting their scope. All percentages in the examples are weight percent unless otherwise indicated.

EXAMPLE 1 - CATALYST PREPARATION

Catalyst C-1, not an embodiment of the invention, is an H-mordenite with a Symmetry Index of 0.88 with a $SiO_2/Al_2O_3$ ratio of 15.2 and 20 weight percent of a silica binder is used without further treatment. This is typical of commercially available mordenite. Its characteristics are given in Table I below.

Catalyst E-1, with a Symmetry Index of 2.1, is selected from commercially available hydrogen mordenites and used without further treatment and has the characteristics listed in Table I below. It also comprises 20 weight percent silica binder.

Catalyst E-2 is prepared by slurrying 300 g of Na-mordenite with a $SiO_2/Al_2O_3$ ratio of 19 and a Symmetry Index of 1.26 with 3000 ml of a 1M HCl solution for 30 minutes at room temperature. The product is washed with three 2000 ml portions of water and dried at 50° C. overnight. The dry solid is stirred in 1500 ml of 6M $HNO_3$ and heated under reflux for two hours. The product is washed with two 2000 ml portions of water and dried at 150° C. in air overnight. The Symmetry Index is 1.68. The characteristics of the catalyst are also listed in Table I below.

Catalyst E-3 is prepared from Na-mordenite with a $SiO_2/Al_2O_3$ ratio of 15 and a Symmetry Index of 0.97 using the procedure described for E-2. The Symmetry Index is 1.38. The characteristics of the catalyst are also listed in Table I below.

Catalyst E-4 has a Symmetry Index of 1.85 and is selected from commercially available hydrogen mordenite and used without further treatment. It has the characteristics listed in Table I below. This catalyst also includes 20 weight percent of a silica binder.

TABLE I

| Catalyst | $SiO_2/Al_2O_3$ (Molar Ratio) | Si/Na (Atomic Ratio) | BET ($m^2/g$) | Micro Pore Volume (ml/g) | Meso-pore Volume (ml/g) | Macro-pore Volume (ml/g) | Total Pore Volume (ml/g) |
|---|---|---|---|---|---|---|---|
| C-1 | 15.2 | 96 | 389 | 0.190 | 0.023 | 0.036 | 0.244 |
| E-1 | 38 | 466 | 489 | 0.180 | 0.080 | 0.034 | 0.294 |
| E-2 | 84 | 1490 | 378 | 0.159 | 0.038 | 0.032 | 0.229 |
| E-3 | 108 | 4200 | 418 | 0.173 | 0.083 | 0.062 | 0.318 |
| E-4 | 156 | 4868 | 389 | 0.160 | 0.139 | 0.324 | 0.624 |

Catalysts C-1 and E-4 are extrudates with a diameter of about 1.5 mm. Catalysts E-1, E-2 and E-3 are crushed filtered particles of about 4 to 5 mm. Catalysts E-1 through E-4 are determined by X-ray diffraction to have Cmcm symmetry having dispersed therein domains of Cmmm symmetry.

Transalkylation to Produce Cumene

The reactant feed is a mixture of distilled heavies from a cumene production and recycled benzene. The feed contains about 61 weight percent benzene: about 9 weight percent p-diisopropylbenzene (DIPB); about 8 weight percent m-DIPB; about 6 weight percent cumene; about 4 weight percent o-DIPB: about 3 weight percent 2-methyl-2-phenylpentane; about 1 weight percent 3-methyl-3-phenylpentane; about 5 weight percent triisopropylbenzene and about 3 weight percent various other impurities.

The pressure is 36 bar and the WHSV (feed weight hourly space velocity) is varied between about 0.4 and 0.8 $hr^{-1}$. Reactor effluent is cooled to room temperature prior to analysis which is performed on line by gas chromatography.

EXAMPLE 2 - TRANSALKYLATION USING CATALYST E-3

In this experiment, the molar ratio of benzene to diisopropylbenzene is 5.9 and the WHSV is either 0.46 $hr^{-1}$ or 0.72 $hr^{-1}$ as shown in the tables below. The temperature is varied and conversion and selectivity are measured at 140° C., 150° C. and 155° C. These results are shown in Table 11 below.

TABLE II

| (CATALYST E-3) | | | | |
|---|---|---|---|---|
| Temperature (°C.) | 150 | 150 | 140 | 175 |
| Conversion (%) | | | | |
| m-DIPB | 59 | 70 | 27 | 75 |
| o-DIPB | 27 | 40 | 16 | 88 |
| p-DIPB | 82 | 86 | 68 | 88 |
| Total | 62 | 70 | 42 | 83 |
| Selectivity (%) | | | | |
| DIPB | 92 | 91 | 92 | 87 |
| Benzene | 102 | 105 | 102 | 114 |
| WHSV ($hr^{-1}$) | 0.72 | 0.46 | 0.46 | 0.46 |
| Time (hrs) | 90 | 60 | 170 | 100 |

The data in Table II demonstrate the long life of the catalyst used in the process of the present invention even in the presence of triisopropylbenzenes. No deactivation is observed when the reaction is run for the cumulative time (420 hr) indicated under the conditions shown.

The amount of specified by-products and of cumene in the feed and effluent are measured. These measurements are done at a WHSV of 0.46 $hr^{-1}$. The results are shown in Table III below.

TABLE III

| (CATALYST E-3) | | | | |
|---|---|---|---|---|
| | Reactor Feed | Reactor Effluent at | | |
| | | 140° C. | 150° C. | 175° C. |
| Ethylbenzene (ppm) | 170 | 50 | 80 | 646 |
| n-propylbenzene (ppm) | — | 90 | 300 | 4722 |
| t-butylbenzene (ppm) | 135 | 915 | 820 | 825 |
| Cumene (wt %) | 4 | 17 | 25 | 28 |

The data above indicate that impurity production increases significantly at higher temperatures.

Using the conditions described above, the transalkylation reaction using Catalyst E-3 is run for a total of about 900 hours. No deactivation is shown over this time period.

EXAMPLE 3 -TRANSALKYLATION USING CATALYST E-2

In this experiment, the molar ratio of benzene to diisopropylbenzene is 5.9 and the WHSV is 0.72 $hr^{-1}$. The temperature is varied and conversion and selectivity are measured at 140° C., 150° C. and 160° C. These results are shown in Table IV below.

TABLE IV

| (CATALYST E-2) | | | |
|---|---|---|---|
| Temperature (°C.) | 140 | 150[1] | 160 |
| Conversion (%) | | | |
| m-DIPB | −5 | 33 | 26 | 63 |
| o-DIPB | 11 | 22 | 18 | 36 |
| p-DIPB | 54 | 70 | 68 | 84 |
| Total | 23 | 46 | 42 | 66 |
| Selectivity (%) | | | |
| DIPB | 95 | 95 | 95 | 93 |
| Benzene | 85 | 98 | 98 | 97 |

TABLE IV-continued (CATALYST E-2)

| Time (hrs) | 120 | — | 210 | 175 |
|---|---|---|---|---|

(1)Slight deactivation is observed at this temperature. The first column represents results at the beginning of the reaction at this temperature and the second column indicates results after 210 hours.

The data in Table IV demonstrate the long life of this catalyst used in the process of the present invention wherein triisopropylbenzenes are present. Slight deactivation is shown at 150° C. In this situation, the conversion of DIPB drops from 46 to 42 percent. At 140° C. and 160° C., no deactivation is observed.

The amount of specified by-products and of cumene in the feed and effluent are measured. These measurements are done at a WHSV of 0.46 hr$^{-1}$. The results are shown in Table V below.

TABLE V (CATALYST E-2)

|  | Reactor Feed | Reactor Effluent at | |
|---|---|---|---|
|  |  | 150° C. | 160° C. |
| Ethylbenzene (ppm) | 20 | 50 | 100 |
| n-propylbenzene (ppm) | <10 | 150 | 560 |
| t-butylbenzene (ppm) | 130 | 840 | 790 |
| s-butylbenzene (ppm) | 40 | 190 | 370 |
| Cumene (wt %) | 4.6 | 18.0 | 24.5 |

EXAMPLE 4 - TRANSALKYLATION USING CATALYSTS E-1 AND E-4

In this experiment, the molar ratio of benzene to diisopropylbenzene is 5.8 and the WHSV is either 0.45 hr$^{-1}$ or 0.74 hr$^{-1}$. The temperature is varied and conversion and selectivity are measured at 150° C. and 175° C. These results are shown in Table VI below.

TABLE VI (CATALYSTS E-4 AND E-1)

| Temperature (°C.) | 150 | 150 | 150 | 150 | 175 |
|---|---|---|---|---|---|
| Catalyst | E-4 | E-4 | E-1 | E-1 | E-4 |
| Conversion (%) |  |  |  |  |  |
| m-DIPB | <1 | 18 | 73 | 73 | 71 |
| o-DIPB | 5 | 14 | 43 | 69 | 66 |
| p-DIPB | 58 | 65 | 87 | 87 | 86 |
| Total | 25 | 37 | 73 | 78 | 76 |
| Selectivity (%) |  |  |  |  |  |
| DIPB | 96 | 94 | 93 | 92 | 91 |
| Benzene | 95 | 99 | 110 | 120 | 110 |
| WHSV (hr$^{-1}$) | 0.74 | 0.45 | 0.75 | 0.45 | 0.74 |
| Time (hrs) | 70 | 110 | 70 | 70 | 110 |

The data in Table VI demonstrate the long life of the catalysts used in the process of the present invention in the presence of triisopropylbenzenes.

The amount of specified by-products and of cumene in the feed and effluent are measured. These measurements are done at a WHSV of 0.46 hr$^{-1}$. The results are shown in Table VII below.

TABLE VII (CATALYSTS E-4 AND E-1)

|  | Reactor Feed | Reactor Effluent at | | | | |
|---|---|---|---|---|---|---|
|  |  | 150° C. | 150° C. | 175° C. | 150° C. | 150° C. |
| Catalyst |  | E-4 | E-4 | E-4 | E-1 | E-1 |
| Ethylbenzene (ppm) | <10 | <10 | 90 | 150 | 140 | 230 |
| n-propylbenzene (ppm) | <10 | 10 | 120 | 510 | 700 | 1210 |
| t-butylbenzene (ppm) | 200 | 1020 | 990 | 870 | 640 | 620 |
| s-butylbenzene (ppm) | <10 | 100 | 140 | 500 | 410 | 560 |
| WHSV (hr$^{-1}$) | — | 0.74 | 0.45 | 0.74 | 0.75 | 0.45 |
| Cumene (wt %) | 5.8 | 13.8 | 17.5 | 28.7 | 28.0 | 29.1 |

EXAMPLE 5 - BROMINE INDEX IN TRANSALKYLATION PRODUCT

Using Catalysts E-1 and E-4 and the procedure described above for the transalkylation reaction, cumene is produced at the temperature and WHSV shown in Table VIII. The bromine index of the cumene is measured using ASTM D-1492-7B. Results obtained are shown in Table VIII below.

TABLE VIII

| Catalyst | Temperature (°C.) | WHSV (hr$^{-1}$) | Bromine Index (mg/100 g) |
|---|---|---|---|
| E-1 | 130 | 0.78 | 3 |
|  | 140 | 0.74 | 5 |
|  | 150 | 0.75 | 2 |
|  | 150 | 0.46 | 3 |
|  | 160 | 0.73 | 3 |
| E-4 | 150 | 0.76 | 2 |
|  | 150 | 0.46 | 5 |
|  | 175 | 0.75 | 12 |

COMPARATIVE EXAMPLE 1 -TRANSALKYLATION USING CATALYST C-1 (NOT AN EMBODIMENT OF THE INVENTION)

Catalyst C-1 is tested using similar conditions and shows significant deactivation after 110 hours of use. The percentage conversion of DIPB drops from about 56 percent to about 15 percent in this time period. The levels of impurities produced at the highest activity are 320 ppm n-propylbenzene, 670 ppm t-butylbenzene and 290 ppm s-butylbenzene.

EXAMPLE 6 - TRANSALKYLATION WITH BENZENE (a) Preparation of Catalyst

A commercial crystalline sodium mordenite is selected with the following properties: a SiO$_2$/Al$_2$O$_3$ molar ratio of 15, a SiO$_2$/Na$_2$O molar ratio of 15, a crystallite size of 1000Å with aggregates ranging in size from 1 micron to 20 microns, a Symmetry Index of 0.97 as determined by X-ray diffraction, and a Langmuir surface area of 303 m$^2$/g. The total pore volume of the sodium mordenite, determined on a Quantachrome Digisorb-6 unit using nitrogen as the adsorbate at 77K, is found to be 0.194 cc/g. The micropore volume, as determined by a t-plot, is found to be 0.046 cc/g. The transitional pore volume, given as the difference (0.194 cc/g - 0.046 cc/g), equals 0.148 cc/g, of which 0.083 cc/g are due to mesopores and 0.065 cc/g are due to macropores.

The sodium mordenite (200g), described hereinabove, is converted to acidic mordenite via exchange with 2000 ml of 1N aqueous hydrochloric acid at room temperature for thirty minutes. The mordenite-acid slurry is maintained homogeneous by agitation during this period, after which the acid-treated mordenite is isolated by filtration. The filtered solid is washed by suspension in 2000 ml of water, refiltered, and dried in air at 100° C. The dried solid is heated to 700° C. in flowing air for 2 hours. The heat-treated acidic mordenite is mixed with 2000 ml of 6N nitric acid and maintained for 2 hours at refluxing temperature under vigorous stirring. After cooling to room temperature the solid is isolated by filtration and washed with water until free of residual acid. The washed solid is dried in air at 110° C. to yield the acidic mordenite catalyst of the invention. Analysis of the catalyst by previously described methods gives the following results: a $SiO_2/Al_2O_3$ molar ratio of 256/1; a $SiO2/Na_2O$ ratio of 3732/1: a Symmetry Index of 1.17: a Langmuir surface area of 673 m²/g: a total pore volume of 0.408 cc/g; a micropore volume of 0.209 cc/g: a mesopore volume of 0.068 cc/g; a macropore volume of 0.132 cc/g: and a ratio of combined meso- and macropore volume to total pore volume of 0.49. The catalyst is activated by heating in air at 700° C. for 2 hours.

(b) Transalkylation

The catalyst (10 g) prepared hereinabove is loaded into a batch reactor with benzene (400 cc), diisopropylbenzene (50 cc) and 1,3,5-triisopropylbenzene (50 cc). The diisopropylbenzene contains about 7.8 weight percent meta isomer, with the balance being essentially para isomer. The 1,3,5-triisopropylbenzene contains about 2.1 weight percent of the 1,2,4-isomer. The reactor is sealed, heated to 250° C. and periodically sampled for up to 20 hours total reaction time with the results shown in Table IX.

TABLE IX

| | Time (hr) | | | | | |
|---|---|---|---|---|---|---|
| | 0 | 1 | 2 | 4 | 6 | 20 |
| Cumene | 1.89 | 10.5 | 18.9 | 30.0 | 37.5 | 52.8 |
| m-DIPB[1] | 3.88 | 13.1 | 17.6 | 16.6 | 14.2 | 3.10 |
| p-DIPB[1] | 45.6 | 29.6 | 18.9 | 9.70 | 7.00 | 1.50 |
| 1,3,5-TIPB[2] | 47.6 | 46.1 | 43.7 | 43.1 | 40.0 | 42.0 |
| 1,2,4-TIPB[2] | 1.00 | 0.97 | 0.94 | 0.90 | 0.90 | 0.90 |

[1]DIPB = Diisopropylbenzene
[2]TIPB = Triisopropylbenzene

It is seen in Table IX that the concentration of p-diisopropylbenzene decreases as a function of time, while the concentration of cumene increases with time. This illustrates the transalkylation of benzene by p-diisopropylbenzene to yield cumene. It is also seen that the concentration of m-diisopropylbenzene increases with time up to about 2 hours as a result of isomerization of the p-diisopropyl isomer. After about 2 hours the concentration of m-diisopropyl isomer also decreases as it is consumed in the transalkylation reaction. It is further seen that the mordenite catalyst does not significantly transalkylate benzene with 1,3,5- or 1,2,4-triisopropylbenzene, therefore the product mixture at 20 hours contains predominantly cumene and essentially the original amount of trialkylbenzene isomers. This mixture can be separated by fractional distillation to yield a fraction of pure cumene, a fraction of residual diisopropylbenzenes which can be recycled to the transalkylation process, and a "bottoms" fraction which is predominantly 1,3,5-triisopropylbenzene.

EXAMPLE 7 -TRANSALKYLATION WITH BENZENE (a) Preparation of Catalyst

A mordenite catalyst is prepared as described in Example 6, with the exception that the acidic mordenite is extracted with 2000 ml of 6N hydrochloric acid instead of nitric acid. The extraction is conducted under reflux conditions at atmospheric pressure for 2 hr. The acid-treated mordenite is filtered and washed with water until free of residual acid, and the resulting acidic mordenite is characterized by a $SiO_2/Al_2O_3$ molar ratio of 73 and a Symmetry Index of 1.42. The mordenite is bound with amorphous silica into 3mm extrudates comprising 20 weight percent binder and 80 weight percent mordenite.

(b) Transalkylation

The mordenite catalyst prepared hereinabove is employed in the transalkylation of benzene by an isomeric mixture of diethylbenzenes and triethylbenzenes. The feed comprises 67.2 percent benzene, 0.87 percent ethylbenzene, 18.84 percent m-diethylbenzene, 8.28 percent p-diethylbenzene, 1.09 percent o-diethylbenzene, 1.43 percent triethylbenzenes, 0.01 percent diphenylethanes, and 2.3 percent residual components. A continuous flow reactor is employed at a temperature of 250° C., a pressure of 36bar, and a weight hourly space velocity of 2.7 1/hr. The product stream contains 56.0 percent benzene, 31.4 percent ethylbenzene, 5.89 percent m-diethylbenzene, 3.00 percent p-diethylbenzene, 0.64 percent o-diethylbenzene, 1.37 percent triethylbenzene, 0.01 percent diphenylethanes, and 2.3 percent residuals. The catalyst is stable for at least about 500 hours. Ethylbenzene and unreacted diethylbenzene are separated by distillation from the triethylbenzenes.

It is seen that the mordenite catalyst catalyzes the transalkylation of benzene by diethylbenzenes to ethylbenzene, while triethylbenzenes are not significantly transalkylated.

EXAMPLE 8 - SEPARATION OF 1,3,5- AND 1,2,4-TRIISOPROPYLBENZENE

A column (1 cc total volume) is packed with a dealuminized aluminosilicate zeolite Y (1 g) having a $SiO_2/Al_2O_3$ molar ratio of 630. A liquid mixture (10 ml) comprising 1,3,5- and 1,2,4-triisopropylbenzenes, wherein the concentration of 1,2,4-triisopropylbenzene is 4 weight percent, is applied to the column. The 1,2,4-isomer is selectively adsorbed on the column, while the 1,3,5-isomer is passed through the column in greater than 99 weight percent purity, as determined by gas chromatography-mass spectrometry techniques.

EXAMPLE 9 -RECOVERY OF CUMENE AND PURE 1,3,5-TRIISOPROPYLBENZENE FROM AN ISOMERIC MIXTURE OF DIISOPROPYLBENZENES AND TRIISOPROPYLBENZENES

Illustrative of the recovery of cumene and pure 1,3,5-triisopropylbenzene from a mixture comprising o-, m-, and p-diisopropylbenzene and 1,3,5- and 1,2,4-triisopropylbenzene is the combined processes of Examples 6 and 8. Thus, benzene is transalkylated with a mixture containing o-, m-, and p-diisopropylbenzenes and 1,3,5- and 1,2,4-triisopropylbenzenes under the conditions of Example 6 to provide a product mixture which is comprised predominantly of cumene and 1,3,5-triisopropylbenzene, and significantly lesser amounts of unreacted diisopropylbenzenes and 1,2,4-triisopropylbenzene. The valuable cumene product and the residual diisopropylbenzenes are separated from the product mixture by fractional distillation. The distillate bottoms containing 1,3,5- and residual 1,2,4-triisopropylbenzenes are passed through a zeolite Y adsorbent as described in Example 8, and pure 1,3,5-triisopropylbenzene is recovered. The zeolite Y adsorbent is regenerated by varying the conditions of the bed until 1,2,4- triisopropylbenzene is removed.

What is claimed is:

1. A process of recovering monoalkylbenzene and pure 1,3,5-trialkylbenzene from an isomeric mixture of trialkyl- and dialkylbenzenes, the process comprising:
   (a) contacting a monocyclic aromatic compound with a transalkylating mixture containing at least one isomer of dialkylbenzene and at least one isomer of trialkylbenzene, wherein the alkyl groups each independently contain from one to about five carbon atoms, the contacting occurring in the presence of an acidic mordenite zeolite catalyst under reaction conditions such that a transalkylation product mixture is obtained containing monoalkylbenzene, 1,3,5-trialkylbenzene, residual amounts of 1,2,4- and/or 1,2,3-trialkylbenzenes, and optionally unreacted dialkylbenzenes, the catalyst being characterized by a $SiO_2/Al_2O_3$ molar ratio of at least about 30:1 and a crystalline structure having a Symmetry Index of at least about 1.0 as determined by X-ray diffraction, and the catalyst showing essentially no deactivation up to at least about 500 hours of use;
   (b) separating monoalkylbenzene, and optionally, unreacted dialkylbenzenes from the transalkylation product mixture;
   (c) contacting the remaining transalkylation product mixture comprising 1,3,5-trialkylbenzene and residual amounts of 1,2,4- and/or 1,2,3-trialkylbenzenes with a zeolite Y aluminosilicate having a $SiO_2/Al_2O_3$ molar ratio of at least about 50:1 under conditions such that the 1,2,4- and/or 1,2,3-trialkylbenzene isomers are selectively adsorbed by the zeolite while the 1,3,5-trialkylbenzene isomer is not significantly adsorbed: and
   (d) collecting the essentially pure fraction of 1,3,5-trialkylbenzene isomer.

2. The process of claim 1 wherein the monocyclic aromatic compound is benzene.

3. The process of claim 1 wherein the transalkylating mixture contains at least one isomer of triisopropylbenzene and at least one isomer of diisopropylbenzene.

4. The process of claim 1 wherein the transalkylating mixture contains at least one isomer of diethylbenzene and at least one isomer of triethylbenzene.

5. The process of claim 1 wherein the acidic mordenite catalyst has a silica/alumina molar ratio of at least about 50:1 and no greater than about 500:1.

6. The process of claim 1 wherein the transalkylation catalyst has a crystalline structure of Cmcm symmetry having dispersed therein domains of Cmmm symmetry, as determined by X-ray diffraction.

7. The process of claim 1 wherein the transalkylation temperature is in the range from about 140° C. to about 300° C.

8. The process of claim 1 wherein a solvent is used in transalkylation.

9. The process of claim 1 wherein a silica binder is employed with the transalkylation catalyst.

10. The process of claim 1 wherein the Zeolite Y adsorbent has a silica/alumina molar ratio in the range from about 50 to about 1000.

11. The process of claim 1 wherein the separation of trialkylbenzene isomers is carried out in the liquid phase.

12. The process of claim 1 wherein the separation of trialkylbenzene isomers is carried out in the gaseous phase.

13. The process of claim 1 wherein a liquid or gaseous desorbent is employed in the separation of the trialkylbenzene isomers.

14. A process of separating 1,3,5-trialkylbenzene from a mixture of the same and 1,2,4- and/or 1,2,3-trialkylbenzene comprising (a) contacting a mixture of 1,3,5-trialkylbenzene and at least one of the 1,2,4- and 1,2,3-trialkylbenzene isomers with an adsorbent bed comprising Zeolite Y aluminosilicate having a silica/alumina molar ratio of at least about 50 under conditions such that the 1,2,4- and/or 1,2,3-trialkylbenzene isomers are selectively adsorbed by the zeolite while the 1,3,5-trialkylbenzene isomer is not significantly adsorbed, (b) collecting the essentially pure fraction of 1,3,5-trialkylbenzene isomer, and (c) varying the conditions of the adsorbent bed such that the 1,2,4- and/or 1,2,3- trialkylbenzene isomers are removed from the bed.

15. The process of claim 14 wherein the trialkylbenzene is triisopropylbenzene.

16. The process of claim 14 wherein the trialkylbenzene is triethylbenzene.

17. The process of claim 14 wherein the Zeolite Y adsorbent has a silica/alumina molar ratio in the range from about 50 to about 1000.

18. The process of claim 14 wherein the trialkylbenzene isomers are in the liquid phase.

19. The process of claim 14 wherein the trialkylbenzene isomers are in the gas phase.

20. The process of claim 14 wherein a liquid or gaseous desorbent is employed.

* * * * *